United States Patent
Dargent et al.

(10) Patent No.: US 6,547,801 B1
(45) Date of Patent: Apr. 15, 2003

(54) GASTRIC CONSTRICTION DEVICE

(75) Inventors: Jerome Dargent, Lyons (FR); Bernard Greillier, Lyons (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 09/786,974
(22) PCT Filed: Sep. 14, 1999
(86) PCT No.: PCT/FR99/02186
§ 371 (c)(1), (2), (4) Date: Jul. 23, 2001
(87) PCT Pub. No.: WO00/15158
PCT Pub. Date: Mar. 23, 2000

(30) Foreign Application Priority Data

Sep. 14, 1998 (FR) .............................. 98 11592

(51) Int. Cl.[7] .............................................. A61B 17/08
(52) U.S. Cl. ..................................................... 606/157
(58) Field of Search ................... 606/151, 153, 606/157, 158

(56) References Cited

U.S. PATENT DOCUMENTS

| | | | | |
|---|---|---|---|---|
| 3,405,432 A | * | 10/1968 | Scaravelli | 24/274 R |
| 3,840,018 A | | 10/1974 | Heifetz | |
| 4,118,805 A | | 10/1978 | Reimels | |
| 4,307,495 A | * | 12/1981 | Sadler | 24/20 R |
| 4,416,267 A | | 11/1983 | Garren et al. | |
| 4,445,254 A | * | 5/1984 | Allert | 24/274 R |
| 4,592,339 A | | 6/1986 | Kuzmak et al. | |
| 4,602,911 A | * | 7/1986 | Ahmadi et al. | 623/2.37 |
| 4,686,747 A | * | 8/1987 | Bakdahl | 24/274 R |
| 4,942,886 A | * | 7/1990 | Timmons | 128/885 |
| 5,160,338 A | * | 11/1992 | Vincent | 600/3 |
| 5,226,429 A | * | 7/1993 | Kuzmak | 128/898 |
| 5,314,437 A | * | 5/1994 | Holtsch | 606/151 |
| 5,356,412 A | * | 10/1994 | Golds et al. | 24/170 |
| 5,383,882 A | * | 1/1995 | Buess et al. | 606/151 |
| 5,571,105 A | * | 11/1996 | Gundolf | 24/21 |
| 5,601,604 A | | 2/1997 | Vincent | |
| 5,683,404 A | * | 11/1997 | Johnson | 606/151 |
| 5,741,283 A | * | 4/1998 | Fahy | 227/902 |
| 5,752,966 A | * | 5/1998 | Chang | 606/151 |
| 5,814,098 A | * | 9/1998 | Hinnenkamp et al. | 33/512 |

FOREIGN PATENT DOCUMENTS

| | | |
|---|---|---|
| DE | 1 541 262 | 6/1969 |
| DE | 197 18 903 A1 | 12/1997 |
| DE | 197 51 733 A1 | 12/1998 |
| EP | 0 876 808 A1 | 11/1998 |
| FR | 2 730 406 A1 | 8/1996 |
| GB | 1174814 | 2/1967 |
| WO | WO 86/04498 | 8/1986 |
| WO | WO 92/02182 | 2/1992 |
| WO | 0611561 A1 | 8/1994 |
| WO | WO 94/27504 | 12/1994 |
| WO | WO 96/01597 | 1/1996 |

* cited by examiner

Primary Examiner—Timothy L. Maust
Assistant Examiner—Khoa D Huynh
(74) Attorney, Agent, or Firm—Oliff & Berridge, PLC

(57) ABSTRACT

Constriction device (1) which can be at least partially implanted in the human or animal body, comprising a constriction member (2) forming a ring in its operational configuration, said constriction member including a flexible band (12), of which the two ends (12a, 12b) are adjacent to one another in the operational configuration, and a means (3) for actuating the constriction member, characterized in that, in cooperation, on the one hand, at least one end (12b) of the flexible band (12) includes a tractile element (13) for moving said end relative to the other end (12a), generating a radial deformation of the constriction member, and, on the other hand, the actuating means (3) comprises a member (25) for pulling the tractile element (13).

14 Claims, 5 Drawing Sheets

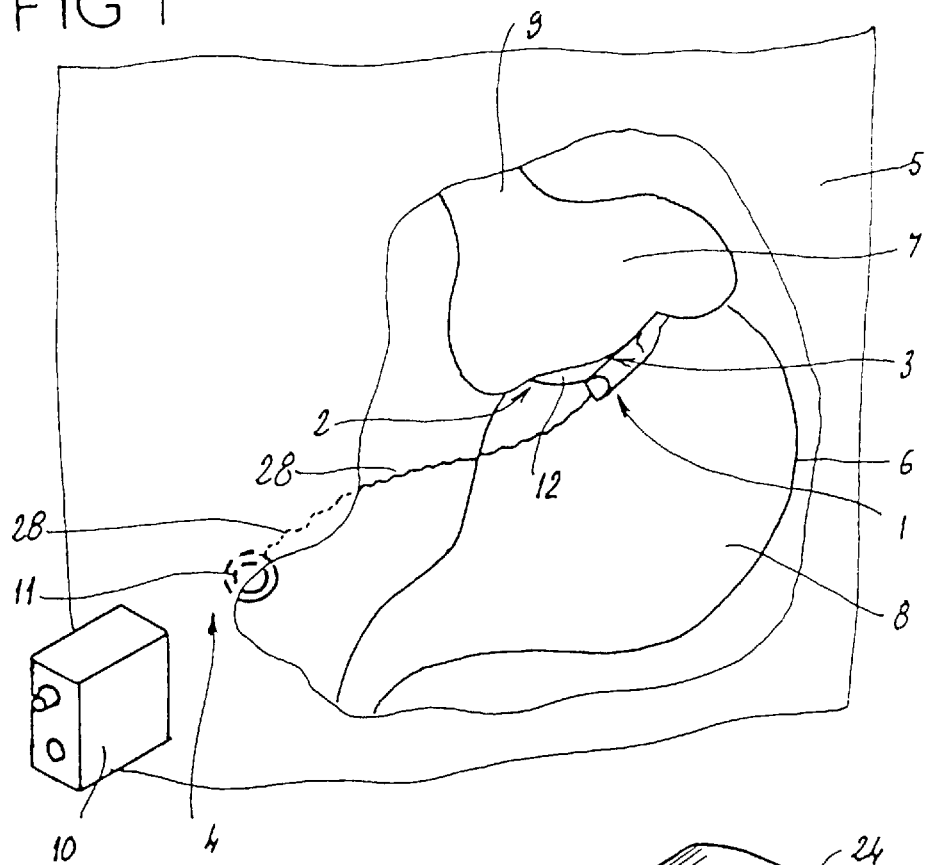
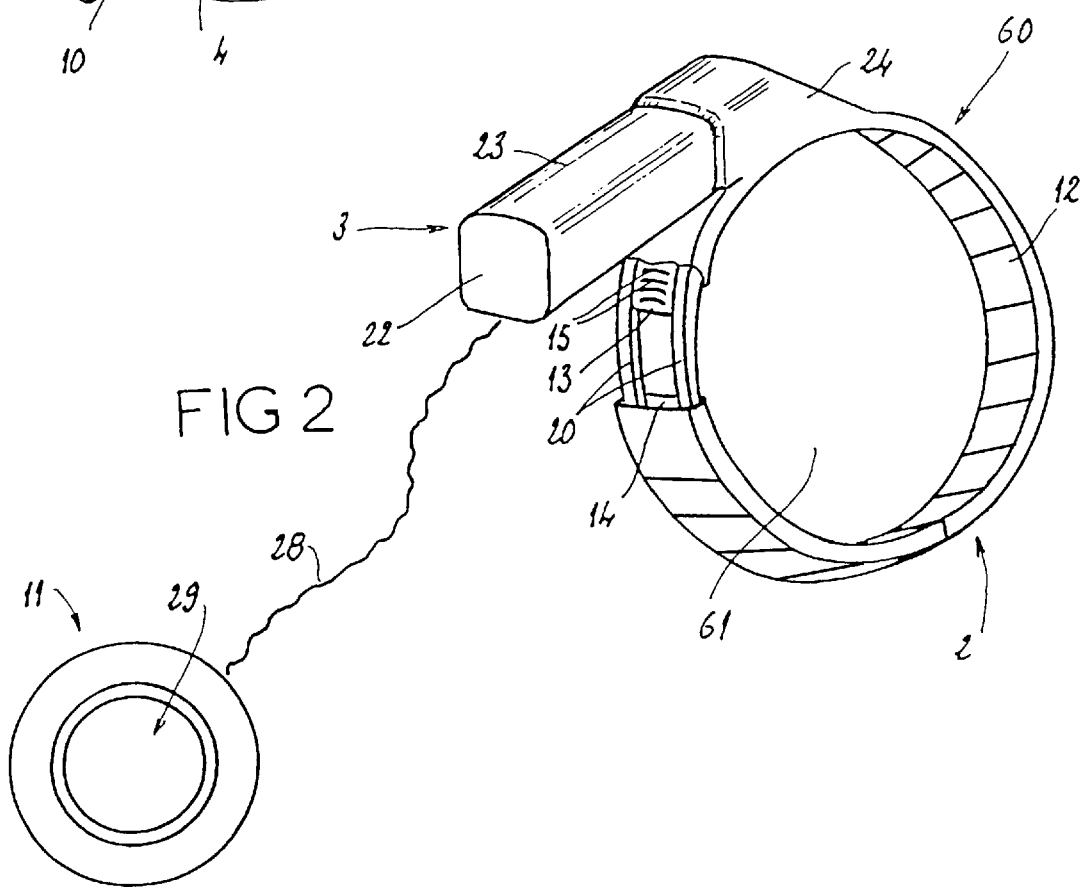
FIG 1
FIG 2

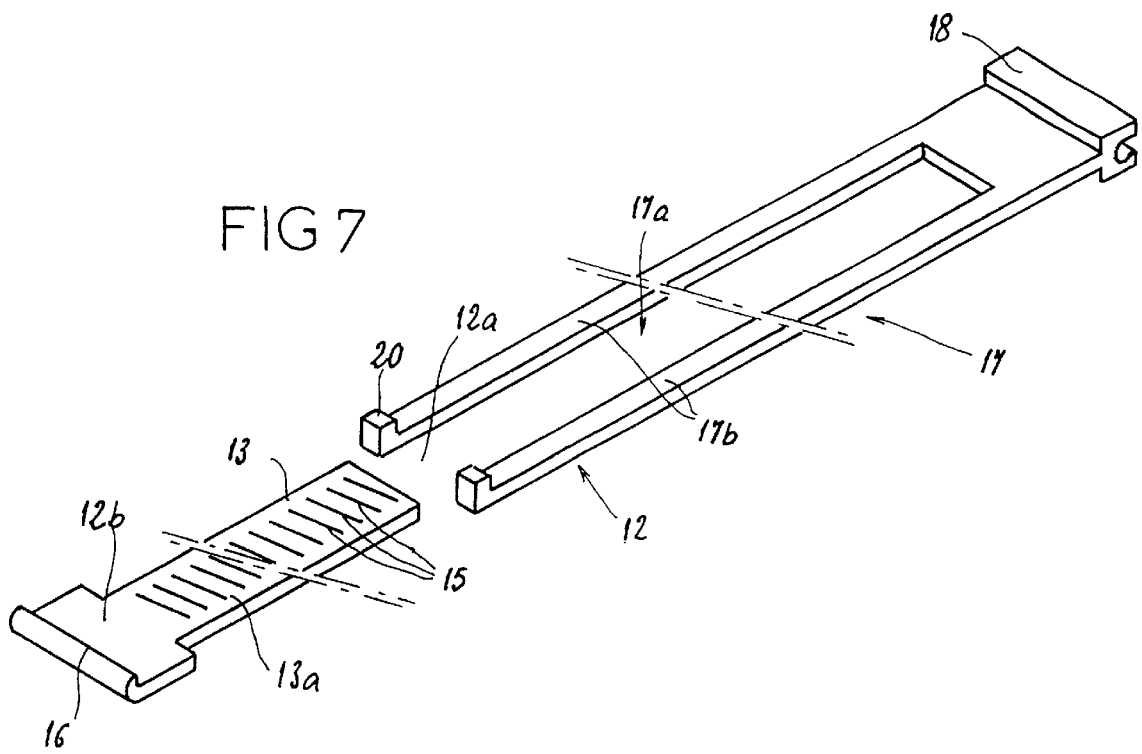

GASTRIC CONSTRICTION DEVICE

The present invention relates to a constriction device which can be at least partially implanted in the human or animal body. The invention will be described more particularly with respect to a gastric constriction device of the "gastroplasty ring" type which can be used for treating morbid obesity.

However, the invention is not limited to such an application or use. The invention is also usefully employed in various medical interventions on humans and animals in which it is necessary to obtain a temporary or permanent constriction, or if appropriate an occlusion, of an organ or conduit or canal.

In the field of gastric constriction, there are several reasons for wanting to control an individual's gastric intake of food, particularly, but not exclusively, in the case of an individual suffering from morbid obesity, or, for example, in cases of diabetes, hypercholesterolemia, or high blood pressure. The expression "morbid obesity" is understood to mean that an individual is at least 45 kg overweight, or at least equal to his ideal weight, as can be defined on the basis of his height and by means of a table for calculating body mass index.

Several surgical techniques are known for trying to treat this obesity, for example by connecting the stomach directly to the small intestine. Another technique consists in placing sutures or staples vertically or horizontally in the stomach wall in order to define a pouch of reduced size compared with that of the stomach, which limits the quantity and speed of transit of the food which can be ingested. However, although these earlier solutions are relatively effective, they are also fairly traumatizing and are rarely if at all reversible, and their feasibility by peritoneoscopy is somewhat uncertain.

Another proposed solution has been to place an inflatable balloon inside the stomach, which gives the patient the constant feeling of being sated. Such a device has been described in patent U.S. Pat. No. 4,416,267. However, fitting balloons of this type has led to a number of not inconsiderable complications, such as intestinal blockages and stomach ulcers, and it takes no account of the risk to the patient associated with prolonged contact of a foreign object with the gastric mucosa.

Finally, a much less traumatizing approach is one in which a gastric constriction device is used comprising firstly a gastric constriction member forming a ring in its operational configuration, for example comprising a flexible band whose two ends are adjacent to one another in the operational configuration, equipped with an inflatable balloon, surrounding the outer wall of the stomach, secondly a means for actuating the gastric constriction member, for example a valve or fluid injector for injecting or introducing said fluid into the balloon, and thirdly a remote control for controlling the actuating means, for example a fluid introduction chamber situated just below the skin at a site relatively easy for the patient to access. The control means and the actuating means are connected via a flexible conduit, for example a catheter, making it possible to transmit the fluid from the chamber to the actuating means. Such a device has the advantage that it can be introduced into the body by peritoneoscopy or laparoscopy, which significantly reduces the trauma and postoperative complications of the surgical intervention compared with "open" surgery, that is to say classical abdominal surgery. However, such a device has the disadvantage that the chamber is quite bulky in the long term. A device corresponding to the above description has been developed by and is known for example from the works of Doctor Kuzmak, and reference may usefully be made to the patents or patent applications WO-A-92/02182, U.S. Pat. No. 4,592,339, EP-A-0611561, WO-A-86/04498, WO-A-94/27504 and U.S. Pat. No. 5,226,429.

However, none of the solutions thus far proposed permits precise control of the degree of gastric constriction. In the case of the devices from Doctor Kuzmak, the volumes of injectable fluid are limited and they represent a solution which is difficult to control with precision. It is possible for a certain volume of fluid to be injected into or withdrawn from the balloon, but the intrinsic elasticity of the latter varies depending on the biological conditions of its implantation, and over the course of time, which makes its expansion difficult to control, and insufficiently adapted to the desired or desirable treatment. Moreover, the manual actuation, for example the patient pressing the subcutaneous push button, or even the accidental actuation of the latter, can have undesirable consequences, for example the need for a repeat intervention, or disinfection of the equipment, etc.

It is known to produce a constriction device which can be at least partially implanted in the human or animal body, comprising a constriction member forming a ring in its operational configuration, said constriction member including a flexible band whose two ends are adjacent to one another in the operational configuration, and a means for actuating the constriction member.

A gastric constriction device with flexible band, implanted and closed on itself about the stomach, is also known from document EP-0876808.

In its operational configuration, the flexible band includes on its inner face a flexible wall which delimits a cavity filled with a variable volume of liquid originating from an equalizing reservoir which is also implanted in the patient's body.

A remote-controlled pump can transmit the liquid from the equalizing reservoir to the gastric band, and vice versa, by way of an electrical control unit. The latter is mounted with the pump in a control housing implanted under the patient's skin.

Besides the disadvantages already mentioned concerning this type of device, there are risks associated with possible leaks of liquid following incorrect manipulation or resulting from manufacturing defects.

Moreover, the inflation of the gastric band promotes the appearance of folds on its inner wall in contact with the stomach. A uniform constriction is thus no longer applied to the periphery of the stomach, and there is an increased risk of pinching the stomach wall in a fold.

The pump is powered by an electrical power source implanted in the body, which can be dangerous depending on the materials constituting such a source, for example an electric battery.

In addition, document U.S. Pat. No. 3,840,018 discloses a device which can be at least partially implanted in the human or animal body, comprising a constriction member forming a ring and a means for actuating this constriction member. The ring which this constriction member forms includes a flexible band, of which at least one of the ends includes a tractile element; the tractile end of the flexible band is moved inside a hollow element of the device via a pulling member which the actuating means comprises. This pulling member is made up of an endless screw with which it is possible to generate a radial deformation of the constriction member.

The document DE 19718903 describes, like the above patent U.S. Pat. No. 3,840,018, all the characteristics set out in the preamble of claim 1.

The present invention proposes a constriction device with which it is possible to overcome the disadvantages of the devices of the prior art and to regulate, in a very precise and reproducible manner, the constriction applied to any organ or conduit of the human or animal body, while avoiding or limiting any surgical intervention required for this control. It is a particular object of the invention to prevent the tractile end of the flexible band from damaging the anatomical environment, in which the device is implanted, when it is moved by the pulling member.

According to the present invention, on the one hand at least one end of the flexible band includes a tractile element for moving said end relative to the other end, generating a radial deformation of the constriction member, and, on the other hand, the actuating means comprises a member for pulling the tractile element. According to an advantageous embodiment of the invention, the tractile element is lamelliform. According to an advantageous embodiment, the flexible band is fixed via one of its ends to the body of the actuating means and includes the tractile element at its other end. Said tractile element comprises pulling means, for example notches, which are able to cooperate with the pulling member of the actuating means.

The device of the present invention is also distinguished by the fact that, in the standby configuration of the constriction member, between these two ends, the flexible band is made up of a first element including a first fixing member, for example male, and a second element including a complementary second fixing member, for example female, the first element being connected to the second element by definitive coupling of the complementary fixing members, in order to obtain the operational configuration of the constriction member.

According to an advantageous embodiment of the constriction device, the fixed end of the flexible band is traversed by a slit, which is longitudinal and open, and is able to receive a tongue, of reduced width, of the tractile element. The constriction member advantageously includes a sheath made of compressible or pliable biocompatible material, enclosing the flexible band. This sheath ensures that the constriction member is biocompatible with the outer wall of the stomach because the gastric constriction device must remain in place for a relatively long period in order to obtain a satisfactory clinical result, and it is therefore preferable to reduce as far as possible the risks of lesions due to contact of a foreign body with the tissues of the stomach wall.

The actuating means advantageously comprises a bi-directional motor coupled to the pulling member.

The pulling member according to the invention meshes with the pulling means in order to move the tractile element in a longitudinal and circumferential direction of the constriction member.

According to an advantageous embodiment, the pulling member is a tangent screw, while the pulling means are regularly spaced notches transverse to the longitudinal direction, and the threading of the tangent screw has the same pitch as that separating the pulling notches.

The constriction device advantageously includes a protective shell which has a part of rigid material forming a motor housing, and a part of compressible or pliable biocompatible flexible material forming the sheath of the flexible band.

The casing and the sheath advantageously form one and the same piece.

The sheath advantageously has material recesses on each side of the flexible band, and/or preformed folds, allowing said sheath to fold in an ordered and regular manner upon radial deformation of the constriction member.

According to an interesting embodiment, the device comprises or is associated with a remote control means. The latter can comprise an extracorporeal emitter and an intracorporeal receiver, the latter having a means for processing a signal emitted by the emitter and for transmitting a control signal to the actuating means. The processing means can comprise a single electric circuit designed to carry both control information and power to the actuating means.

The processing means can advantageously comprise an electric circuit consisting of a resonance induction coil, a rectifier, a pulse generator, at least one shift register circuit, and a circuit for controlling the direction of running of the actuating means.

By way of example, according to the invention the receiver of the control means is arranged remote from the constriction member and is connected electrically to the actuating means.

According to another advantageous illustrative embodiment of the device according to the invention, the extracorporeal emitter comprises an electric circuit made up of an electrical power supply, an oscillator, an amplifier circuit and a primary induction coil.

The emitter can additionally comprise at least one member for selecting the frequency of the oscillator.

The constriction device according to the invention is also distinguished by the fact that the actuating means is designed to retain, in a stable manner, the mutual relative position of the two ends of the flexible band in the absence of power supply to said actuating means.

The present invention will be better understood from the following detailed description of a preferred embodiment, accompanied by the attached drawing in which:

FIG. 1 is a diagrammatic perspective view, partially cut away, of the abdomen of the human body in which part of a gastric constriction device according to the invention has been implanted;

FIG. 2 is a perspective view, partially cut away, of the part of the gastric constriction device according to the invention which can be implanted in the human body;

FIG. 7 is a perspective view, developed and shown flat, of the flexible band belonging to the constriction member represented in FIGS. 2 to 4.

Figure 3:
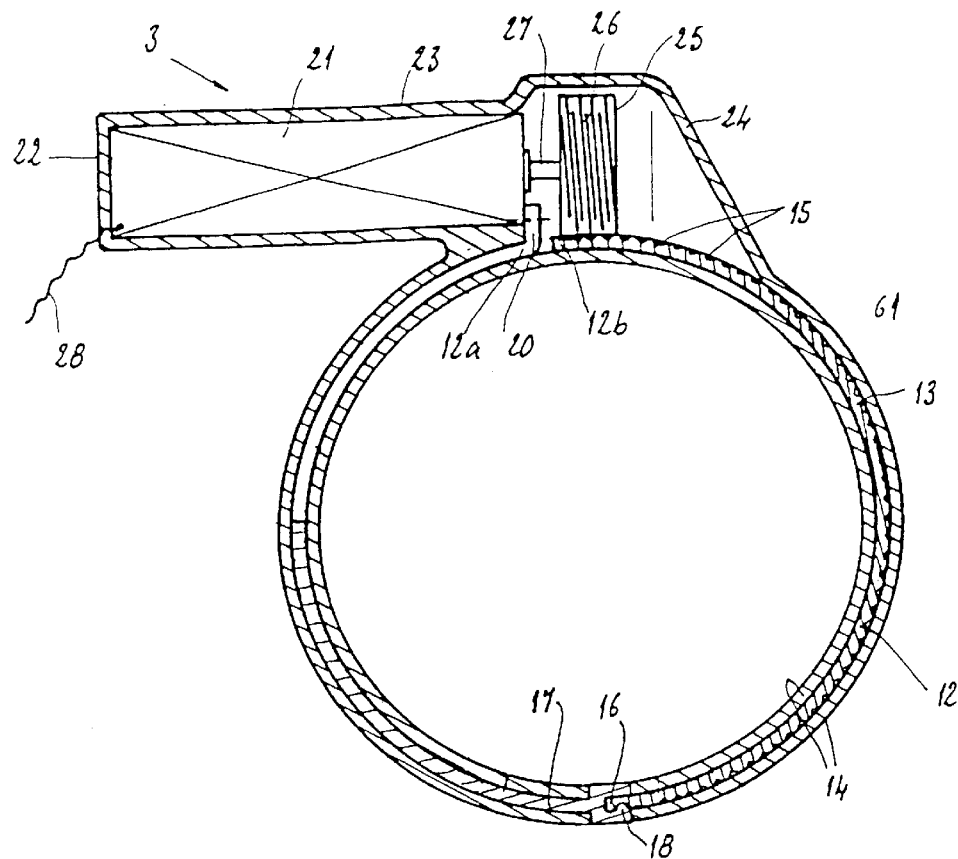
FIG. 3 is a cross section of the gastric constriction member, in its operational configuration, and of the means for actuating a device according to the invention; the constriction member is represented in the nondeformed state, with a maximum transverse section of the constriction ring.

Referring now to FIG. 1, the constriction device, in particular gastric constriction device, according to the invention is indicated in general by reference number 1. This device comprises a gastric constriction member 2 which substantially forms a constriction ring of variable transverse section 61, a means 3 for actuating the gastric constriction member 2, and a means 4 for remote control of the actuating means 3.

The gastric constriction device 1 is partially implanted in the body 5, represented diagrammatically, and the constriction member 2 forms a ring surrounding the outer wall of the stomach 6 in such a way as to create a small upper pouch 7 and a lower pouch 8 which is larger than the upper pouch. The movement of food from the esophagus 9 is limited on the one hand by the restricted volume of the upper pouch 7 and on the other hand by the degree of constriction applied by the constriction member 2. Thus, and in a generally known manner, the intake of food is controlled in order, for example, to help a person suffering from morbid obesity to lose weight.

The control means 4 comprises an emitter 10 and a receiver 11, the receiver 11 including a means for processing a signal emitted by the emitter 10 and for transmitting a control signal to the actuating means 3 so as to be able to regulate with precision the degree of constriction of the constriction member 2. The emitter 10 and the receiver 11, and the means constituting these, will be described in more detail below. The receiver 11 of the control means 4 is arranged at a distance from the constriction member 2 and is connected electrically to the actuating means 3 via a wire 28.

According to the present invention, and as is represented in FIG. 2, the constriction member 2 comprises a flexible lamelliform band 12, for example made of polyethylene or polypropylene, and a sheath 14 made of compressible or pliable biocompatible flexible material, for example silicone, enclosing a flexible band 12. This sheath makes it possible to reduce the trauma suffered by the outer wall of the stomach during the movements of the latter against the constriction member 2 during passage of food from the upper pouch 7 to the lower pouch 8. Given that the diameter formed by the flexible band 12 varies as a function of the gastric constriction to be applied by way of the actuating means 3, it is preferable for the sheath 14 to be made of a compressible or pliable material so that it does not impede this increase or reduction in the transverse section 61 of constriction.

The flexible band can be of a shape other than lamelliform, for example of circular cross section.

Figure 4:
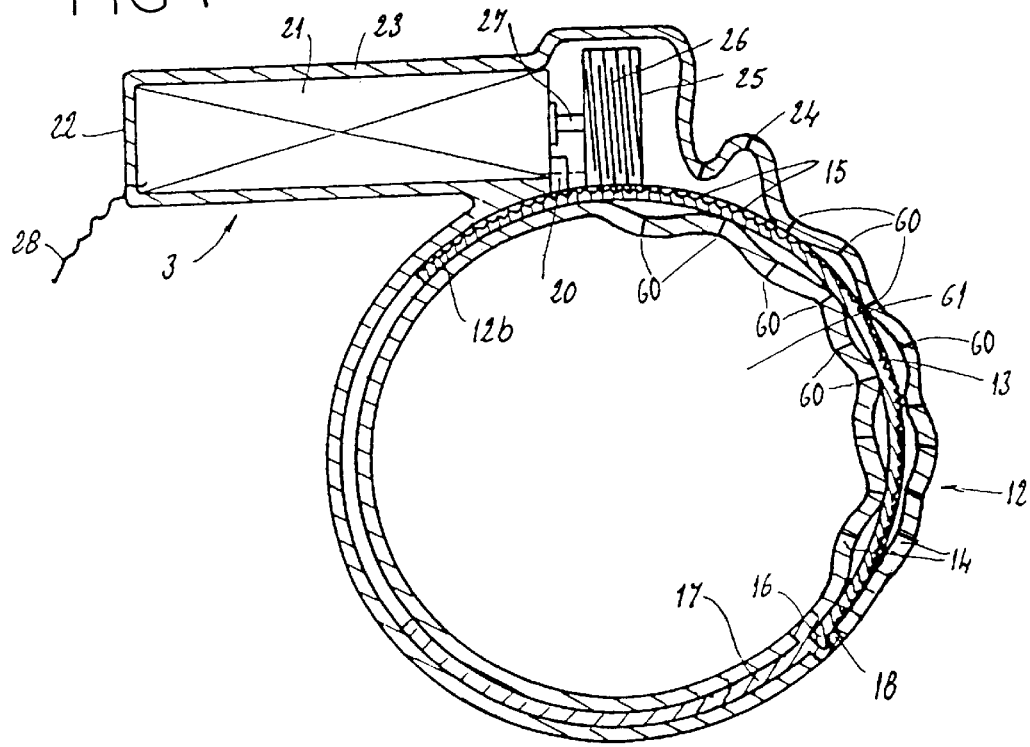
FIG. 4 is a cross section through the constriction member in FIG. 3 during actuation; the constriction ring has a reduced transverse section compared with that shown in FIG. 3.

As is represented in FIGS. 2 to 4, in the operational configuration of the constriction device, and as will be better understood with reference to FIG. 7, the flexible band 12 has a loop-shaped configuration whose two ends 12a and 12b, or end strands, are fixed (12a) and mobile (12b) on a predetermined trajectory. In general, the two ends 12a and 12b are and remain adjacent to one another, overlapping or superposing one another on a trajectory of relative movement, linear but curved, for example circumferential, but concentrically relative to one another, according to the desired degree of constriction, and this by way of the actuating means 3 which will be described below.

In order to move the mobile end 12b relative to the fixed end 12a, the former includes a tractile element 13, which is itself lamelliform, and the actuating means 3 comprises a member 25 for pulling the tractile element in order to move the mobile end 12b of the flexible band 12 relative to the fixed end 12a, thus generating a radial deformation of the constriction member 2, and more exactly a variable transverse section 61 of constriction.

The end 12a of the flexible band 12 is fixed by a means 20 to the body of the actuating means 3, and the tractile element 13, toward the free end 12b, comprises pulling means, for example notches 15 which can cooperate with the pulling member 25.

As is represented in FIG. 7, the fixed end 12a of the flexible band 12 is traversed by a longitudinal and open slit 17a which is able to receive a tongue 13a, of reduced size, of the tractile element 13. The developed length of the slit 17a is adapted to the travel of the end 12b relative to the end 12a on the trajectory of overlap, namely in the present case the trajectory of insertion of the free end 12b into the fixed end 12a.

In an advantageous embodiment according to the invention, the sheath 14 can have extensile properties so as to improve contact with the organ subjected to the constriction. It is then possible to start from an initial position, without constriction, of the flexible band 12, in which the sheath 14 is tensioned. Upon constriction, the sheath 14 then follows the retracted shape of the flexible band 12 and contracts.

The element 13 at the end 12b can be pulled by the pulling member 25 so that it can be moved in two opposite circumferential longitudinal directions, namely a direction of reduction of gastric constriction, and a direction of increase of gastric constriction. Thus, the tractile element 13, as is shown diagrammatically in FIG. 2, preferably has pulling notches 15 arranged substantially transverse to the longitudinal direction of the tractile element 13 and regularly spaced apart from one another at a predetermined pitch and, by cooperation with the pulling member 25 consisting of an endless screw, make it possible to move the element 13 in a direction of reduction of gastric constriction or, conversely, in an opposite direction. The pulling notches 15 can be present in other forms, for example slots, recesses or teeth, the main point being that they can cooperate or mesh with the corresponding pulling member 25 provided on the actuating means 3.

Moreover, according to the preferred embodiment of the invention, and as is illustrated in FIG. 3, in a standby configuration of the constriction member 2, the flexible band 12 is made up of a first element 13 including a first fixing member 16, for example male, and a second element 17 including a complementary second fixing member 18, for example female, the first element 13 being connected to the second element 17 by definitive coupling of the complementary fixing members 16, 18. This arrangement makes it possible in particular to modulate the length of the flexible band 12, for example in order for it to adapt to a greater gastric constriction diameter, which may be the case in particular if one wishes to create an upper pouch 7 of a volume equivalent to the lower pouch 8.

The division of the flexible band 12 into two elements or branches 13 and 17 which can be coupled together greatly facilitates positioning of the constriction member 2 around the stomach, since in this case the ends of the elements 13 and 17 are coupled after said elements have been passed round the stomach in the surgical intervention.

As is shown in FIGS. 3, 4 and 7, the free end 12a of the flexible band 12, corresponding to the second element 17, is traversed over the greater part of its length, and opposite its end bearing the female connection member 18, by a longitudinal and open slit 17a which is able to receive a tongue 13a, of reduced width, of the tractile element 13. This part or tongue 13a is of reduced width, at least along the length of overlap of the ends 12a and 12b. The slit 17a is bordered by two wings 17b whose ends are bent at 20 in order to form a means of attachment to the body of the actuating means 3.

The actuating means 3 comprises a bi-directional electric motor 21 which is housed in a protective shell 22 having a part 23 made of rigid material forming a motor casing, and a part 24 made of compressible or pliable biocompatible flexible material forming the sheath 14 of the flexible band 12. The shell 22 can be made, and preferably is made, entirely as one and the same piece of biocompatible material, for example silicone, the hardness or stiffness of the material being suitably chosen to produce the rigid casing and the flexible sheath. This shell 22, obtained for example by molding, ensures lead tightness with respect to biological fluids which could otherwise penetrate into the motor casing and lead to malfunctioning of the latter or produce chemical reactions with the components of the motor 21, with a deleterious effect on the patient. Advantageously, the sheath 14 has material recesses and/or preformed folds (shown representatively as fold lines 60) on each side of the flexible band 12 which allow the sheath 14 to fold in an ordered and regular manner during actuation of the constriction member 2 and to do so along and around the band 12 whose length diminishes according to the traction on the free end 12b of the band 12. This also prevents excessive mechanical constraint on the motor 21 of the actuating means 3 and makes it possible at the same time to overcome the resistance to folding of the constriction member.

The motor 21 is connected in rotation to the pulling member 25 cooperating with the notches 15 of the tractile element 13. In the embodiment in FIGS. 3 and 4, this member 25 is a tangent screw 15 wedged on the output shaft 27 of this motor 21, and whose threading 26 meshes with the notches 15. To reduce the overall size, the longitudinal axes of the screw 25, shaft 27 and motor 21 are substantially in the transverse median plane of the ring of the constriction member 2. The motor 21 is connected electrically to the intracorporeal receiver 11 of the control means 4 by way of one or more electric wires 28.

Arranged between the motor 21 and the pulling member 25 there is a reducing gear (not shown) with a considerable demultiplication ratio.

Thus, the actuating means 3 is designed to maintain, in a stable manner, the mutual relative position of the two ends 12 and 12b of the band 12 in the absence of power supply to said actuating means 3.

The return forces to which the band 12 is subjected do not permit rotation of the motor 21, the rotations of which determine the degree of constriction in the embodiment of the constriction device according to the invention.

When the constriction device has been implanted in the body of a patient and the flexible band 12 has been closed in its operational configuration, for example by coupling of the complementary fixing members 16, 18, the band is in substantially the shape of a ring, as is represented in FIG. 3. The first pulling notches 15 of the tractile element 13 are meshed with the threading 26 of the screw 25 so as to maintain the ring shape of the constriction device 2.

FIG. 4 shows the configuration of the constriction member 2 after the control means 3 have been activated to reduce the diameter of the flexible band 12 and thus increase gastric constriction. It will be noted that the sheath 14, which is made of flexible material, has folded, which allows the tongue 13a of the tractile element 13 to penetrate into the slit 17a of the end 12a during the displacement which is imparted to it by the screw 25.

Figure 5:
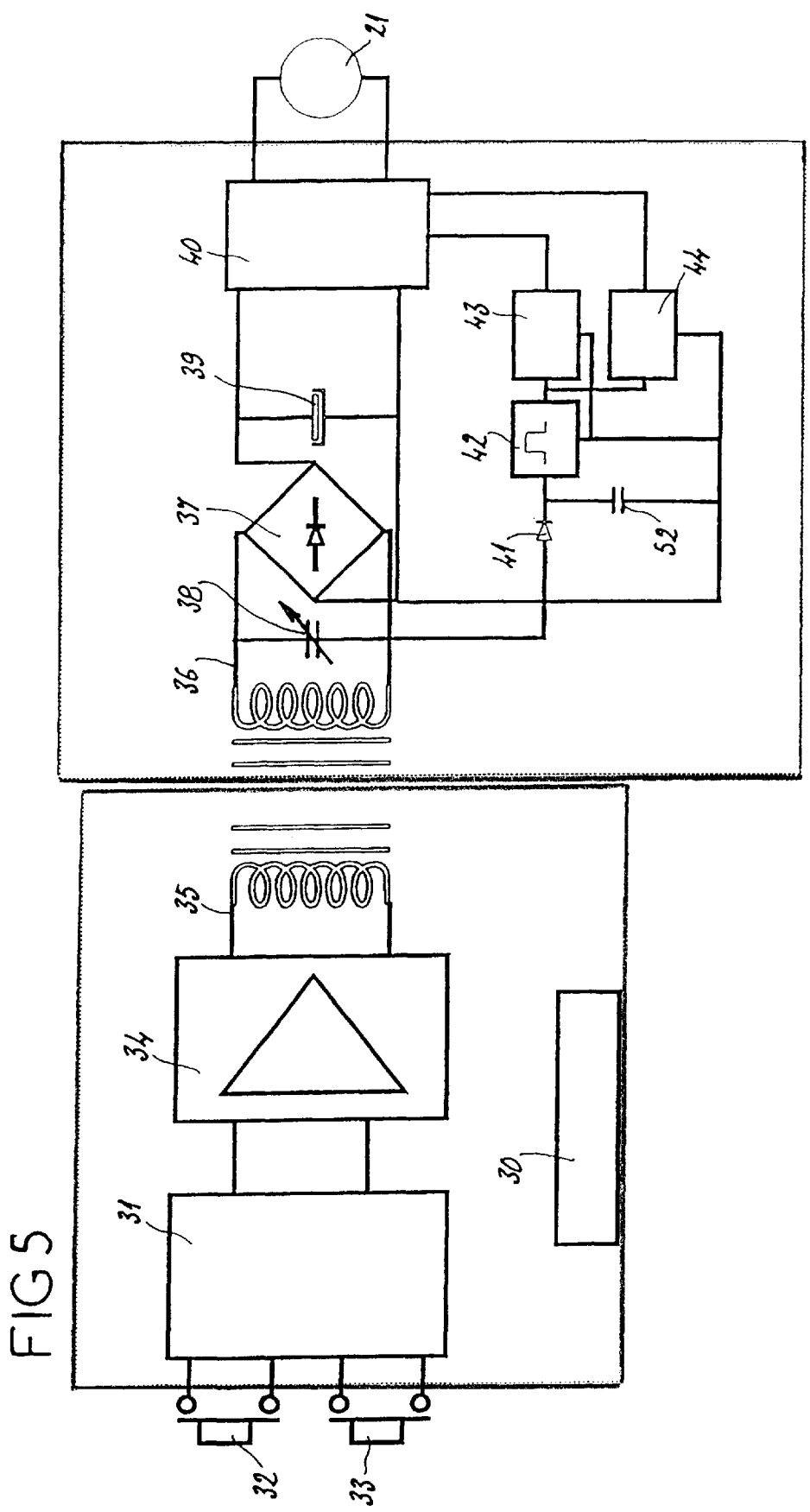
FIG. 5 is a diagrammatic view of the electric circuits of the means for remote control of a gastric constriction device according to the invention.

The control means 4 will now be described with useful reference to FIG. 5. In the preferred embodiment of the invention, the control means comprises an extracorporeal emitter 10 and an intracorporeal receiver 11, for example implanted under the skin, for example at the lower limit of the sternum, or in another suitable location. The receiver includes a means 29 for processing a signal emitted by the emitter 10 and for transmitting a signal for controlling the actuating means 3. This signal processing and transmitting means 29 can also be arranged near or on the actuating means 3, for example on the shell 22 of the motor 21.

In the preferred embodiment, the extracorporeal emitter 10 is made up of an electric circuit including a electrical power source 30, for example a battery, feeding an oscillator 31 with three frequencies, namely a charging frequency F1, a forward operation frequency F2, and a reverse operation frequency F3. The oscillator 31 is connected, on the one hand, to two control buttons for forward operation 32 and reverse operation 33, respectively, and, on the other hand, to an amplifier circuit 34. The amplifier circuit 34 is connected to a resonance coil 35 which preferably has a relatively large diameter in relation to the receiver 11, for example about 30 cm. The resonance coil 35 can be a toroid coil of copper or gold wire placed in a ring of silicone (not shown) and it resonates at an operating frequency, corresponding to one of the three frequencies mentioned above, when the circuit is powered from the power supply 30.

When the emitter 10 is tensioned, the oscillator 31 emits a first frequency F1 for charging the circuit, which is amplified by the amplifier 34 and sent to the resonance coil 35 and which supplies power to the receiver 11. The latter includes a frequency induction coil 36, preferably about 3 cm in diameter, and functioning at a frequency of about 1 MHz. The induction coil 36 is connected to a diode bridge 37 and to a tuning capacitor 38 which regulates the resonance frequency of the receiver circuit. The diode bridge 37 is connected to an electrolytic capacitor 39 making it possible to store sufficient energy to charge and actuate the various circuits of the receiver, and to an adapter circuit 40 for driving the motor 21. The signal received by the resonance coil 36 in the form of energy passes via the diode bridge 37 which rectifies and filters the signal and which thus provides a source of power for the motor and the electric circuits of the receiver. The tuning capacitor 38 is connected via a signal detection diode 41 to a circuit 42 for shaping the frequency received from the tuning capacitor.

Figure 6:
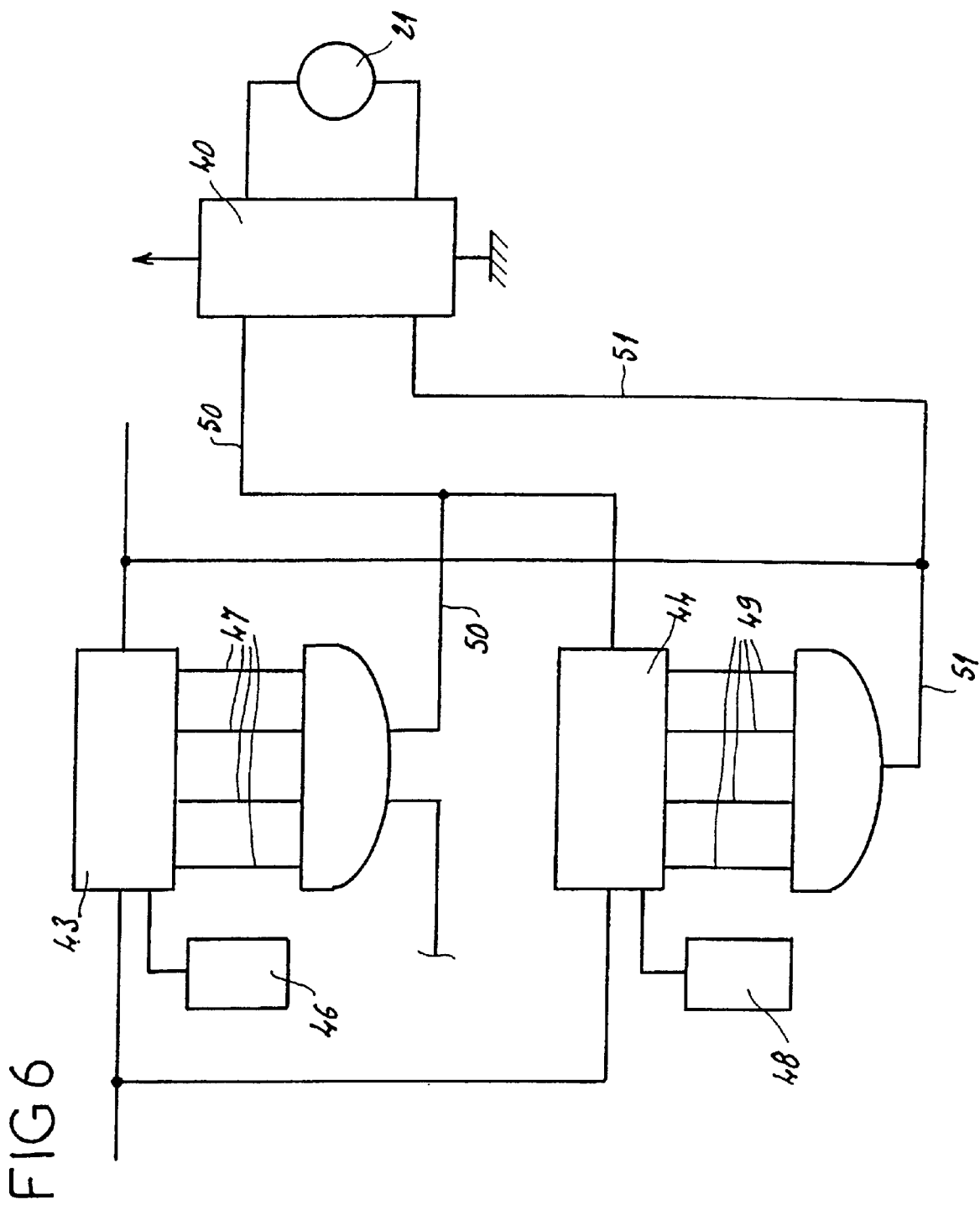
FIG. 6 is a more detailed diagrammatic view of one of the electric circuits in FIG. 5.

FIG. 6 shows diagrammatically the circuit for processing the frequency shaped and transmitted in pulse form. This signal is transmitted to two shift register circuits 43, 44, for example of the FSK type, a first shift register circuit 43 being programmed to filter a forward operation frequency F2, and a second shift register circuit 44 being programmed to filter a reverse operation frequency F3. The first shift register circuit 43 includes an oscillator 46, shifting each pulse received in AND gates 47 after a predetermined time set to the forward operation frequency. The second shift register circuit 44 also includes an oscillator 48, shifting each pulse received in AND gates 49 after a predetermined time set to the reverse operation frequency. Thus, these two circuits 43, 44 measure the recurrence of the pulse supplied via the shaping circuit 42. The shift register circuits end in two outlets 50, 51 connected to the adapter 40 for driving the motor, one triggering driving in the forward direction, the other triggering driving in the reverse direction. In order to avoid surrounding frequency interference, the emitter 11 can also be provided with a bypass capacitor 52 placed between the tuning capacitor 38 and the frequency-shaping circuit 42. It should be noted that all the electric circuits of the receiver which have been described above could also be integrated in a microelectronic circuit, or an electronic chip, and this chip could then be placed or fixed on the actuating means 3.

The functioning of the receiver circuit will now be described with reference to the above description. If the operator presses the forward operation button 32 of the emitter 10, the frequency F2 is emitted, amplified, then induced in the circuit of the receiver 11. This frequency F2 is detected by the first shift register circuit 43 as being the forward operation frequency, as a result of which the adapter circuit 40 turns the motor 21, the shaft 27 and the drive means 25 in such a way that the latter advances the tractile element 13 in the direction of the motor, thereby reducing the diameter of the band 12. When the operator presses the reverse operation button 33 of the emitter 10, the reverse effect is produced and the diameter of the band 12 is increased.

It is thus possible to regulate the internal dimension of the gastric constriction member in a very precise manner and without any physical manual intervention on the elements implanted in the body. This permits a procedure better adapted to the needs of the patient to be treated, and simpler manipulations, since the gastric constriction applied can be modified simply by bringing the emitter 10 in front of the receiver 11 and actuating it.

Alternatively, when the constriction is regulated directly via the percutaneous route by the surgeon using suitable instruments, the actuating means 3 does not include a motor, and makes it possible to obtain stable and irreversible control of the constriction.

What is claimed is:

1. A gastric constriction device which is at least partially implanted in a human or animal body, comprising a constriction member (2) forming a ring having a maximum transverse section in its operational configuration, said ring including a flexible band (12) having a mobile end and a fixed end, the two ends (12a, 12b) are adjacent to one another in the operational configuration, corresponding to the maximum transverse section of said ring, the mobile end (12b) of the flexible band (12) includes a tractile element (13), and a means (3) for actuating the ring-forming member (2) to pull the tractile element, and to move said mobile end (12b) relative to the fixed end (12a), generating a radial deformation of the constriction member, wherein the fixed end (12a) of the flexible band (12) is traversed by a longitudinal and open slit (17a) which is bordered by two wings (17b), said slit receiving, in an overlapping manner, a reduced width curved tongue (13a) of the tractile element (13), further wherein the relative and concentric movement of the mobile end into the fixed end regulates the transverse section of the flexible band, causing the ring-forming member to form the gastric constriction device.

2. The gastric constriction device (1) as claimed in claim 1, characterized in that the constriction member (2) includes a sheath (14) made of compressible or pliable biocompatible material, enclosing the flexible band (12).

3. The gastric constriction device (1) as claimed in claim 2, characterized in that it includes a protective shell (22) which has a part (23) of rigid material forming a housing for the means for actuating (3), and a part (24) of compressible or pliable biocompatible flexible material forming the sheath (14) of the flexible band (12).

4. The gastric constriction device (1) as claimed in claim 3, characterized in that the protective shell and the sheath (14) form one and the same piece.

5. The gastric constriction device (1) as claimed in claim 2, characterized in that the sheath (14) has at least one of material recesses and preformed folds on each side of the flexible band (12), allowing said sheath to fold in an ordered and regular manner upon radial deformation of the constriction member (2).

6. The gastric constriction device (1) as claimed in claim 1, characterized in that, in a standby configuration of the constriction member (2), between its two ends, the flexible band (12) is made up of the tractile element (13) including a complementary first fixing member (16), and a second element (17) including a complementary second fixing member (18), the tractile element (13) being connected to the second element (17) by definitive coupling of the-complementary fixing members (16, 18), in order to obtain the operational configuration of the constriction member (2).

7. The gastric constriction device (1) as claimed in claim 1, characterized in that it comprises or is associated with a remote control means (4).

8. The gastric constriction device (1) as claimed in claim 7, characterized in that the remote control means (4) comprises an extracorporeal emitter (10) and an intracorporeal receiver (11), the receiver having a means (29) for processing a signal emitted by the emitter (10) and for transmitting a control signal.

9. The gastric constriction device (1) as claimed in claim 8, characterized in that the processing means (29) comprises a single electric circuit designed to carry both control information and power to the means for actuating (3).

10. The gastric constriction device (1) as claimed in claim 8, characterized in that the processing means (29) comprises an electric circuit consisting of a resonance induction coil (36), a rectifier (37), a pulse generator (42), at least one shift register (43, 44), and a circuit (40) for controlling the direction of running of the actuating means.

11. The gastric constriction device (1) as claimed in claim 8, characterized in that the receiver (11) of the remote control means (4) is arranged remote from the constriction member (2) and is connected electrically (28) to the means for actuating (3).

12. The gastric constriction device (1) as claimed in claim 8, characterized in that the extracorporeal emitter (10) comprises an electric circuit made up of an electrical power supply (30), an oscillator (31), an amplifier circuit (34) and a primary induction coil (35).

13. The gastric constriction device (1) as claimed in claim 12, characterized in that the emitter (10) additionally comprises at least one member (32, 33) for selecting the frequency of the oscillator (31).

14. The gastric constriction device (1) as claimed in claim 1, characterized in that the actuating means (3) is designed to retain, in a stable manner, the mutual relative position of the two ends (12a, 12b) of the flexible band (12) in the absence of power supply to said actuating means (3).

* * * * *